United States Patent [19]
Barney

[11] Patent Number: 5,800,171
[45] Date of Patent: Sep. 1, 1998

[54] EXHAUST CONTROL SYSTEM FOR PNEUMATIC DEVICES AND METHOD

[76] Inventor: Everett A. Barney, 17100 S. Point Dr., Nehalem, Oreg. 97131

[21] Appl. No.: 574,335

[22] Filed: Dec. 18, 1995

[51] Int. Cl.$^6$ .................................................. A61C 1/05
[52] U.S. Cl. ........................................ 433/132; 433/91
[58] Field of Search .......................... 433/132, 91, 92, 433/95, 98; 415/169.2, 904

[56] References Cited

U.S. PATENT DOCUMENTS

| | | | |
|---|---|---|---|
| 3,092,908 | 6/1963 | Flatland | 433/132 |
| 3,988,134 | 10/1976 | Gandrud | 55/319 |
| 4,564,374 | 1/1986 | Hofmann | 55/57 |
| 4,684,345 | 8/1987 | Cattani | 433/92 |
| 4,917,603 | 4/1990 | Haack | 433/91 |
| 5,011,519 | 4/1991 | Maeda | 55/216 |
| 5,074,787 | 12/1991 | Tsukada | 433/98 |
| 5,122,153 | 6/1992 | Harrel | 433/91 |
| 5,338,194 | 8/1994 | Strohmaier | 433/82 |
| 5,342,196 | 8/1994 | Van Hale | 433/82 |
| 5,374,189 | 12/1994 | Mendoza | 433/132 |

*Primary Examiner*—John J. Wilson
*Attorney, Agent, or Firm*—Kolisch, Hartwell, Dickinson, McCormack & Heuser

[57] ABSTRACT

An exhaust control system and method are provided for use with one or more pneumatic devices so as to draw contaminated fluid from the fluid outputs of such devices and deposit such contaminated fluid in a waste collector such as a drain. The system is configured for use with any conventional pneumatic device of the type which includes a pressurized fluid input, a turbine driven by fluid from such input, and a fluid output which exhausts fluid from the turbine. Fluid is directed from the fluid output of each pneumatic device to an exhaust manifold which includes a number of inflow ports corresponding to the number of devices serviced. The inflow ports connect to a depressurization chamber, where the fluid flow pressure is lowered, and from which the fluid is drawn via a collective outflow port. The fluid is drawn from the exhaust manifold using a vacuum source and then directed to a waste collector such as a drain.

20 Claims, 1 Drawing Sheet

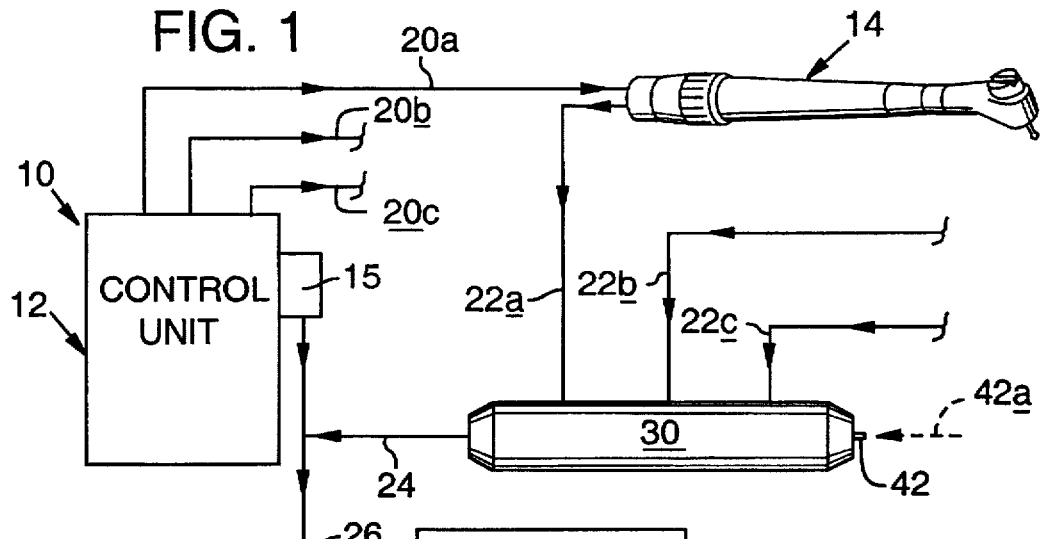
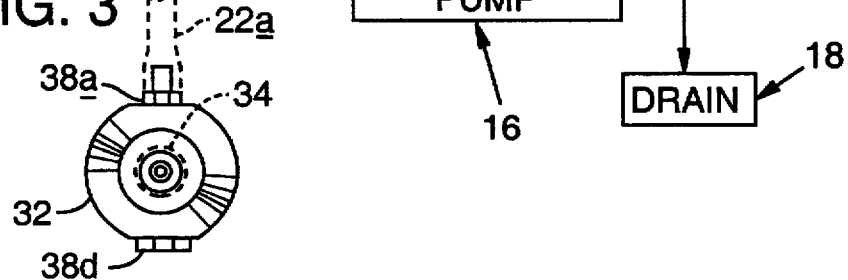
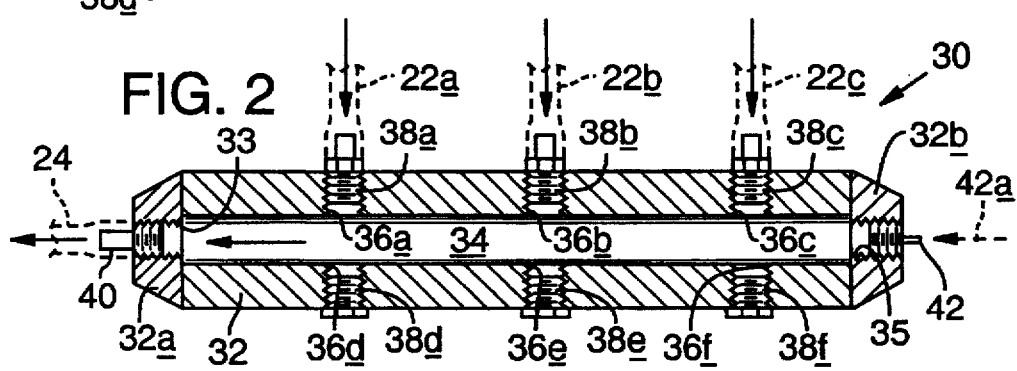
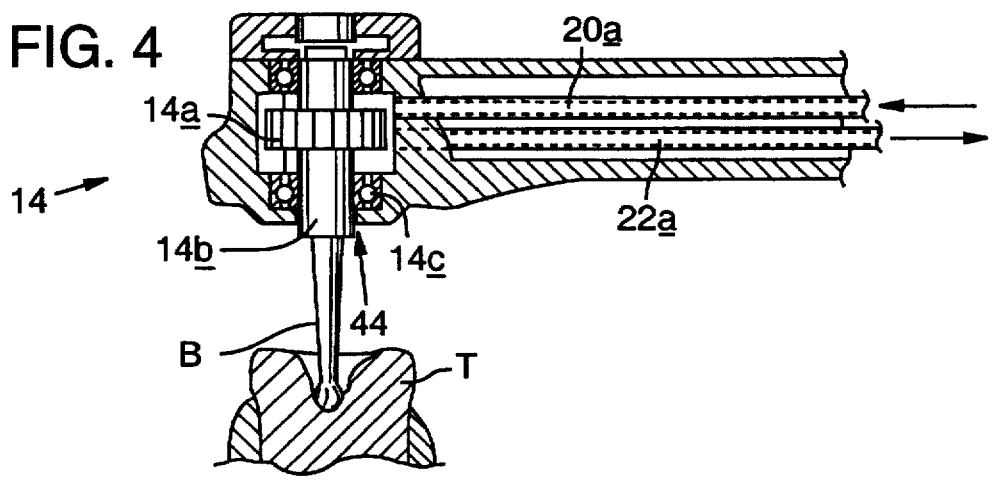

EXHAUST CONTROL SYSTEM FOR PNEUMATIC DEVICES AND METHOD

TECHNICAL FIELD

The present invention relates generally to pneumatic devices, and more particularly, to an exhaust control system for use in collecting fluid expelled by pneumatic devices. Although the invented exhaust control system has broad utility, it is particularly well suited for use in controlling exhaust from pneumatic tools of the type employed by dentists, and the invention will be described in that context below.

BACKGROUND ART

For many years now, dentists and dental technicians have utilized dental units fitted with pneumatic tools which are specially configured to treat and repair teeth. Such tools, known as handpieces, typically include a dental bit mounted on a fluid-driven turbine which rotates at extremely high speeds. The turbine is powered by an air compressor which supplies fluid (i.e., pressurized air) to the turbine, thereby turning both the turbine and the associated dental bit. As the air passes through the turbine, it is contaminated with turbine lubricants, and potentially with bacteria, viruses or pathogens drawn from the air compressor, or from the patient's mouth through leaks or openings in the handpiece. Conversely, turbine lubricants may be released through such openings into the patient's mouth. The contaminated air is expelled through an output, often directly into the dentist's office. Conventional dental units thus have proven inadequate due to the generally unhygienic environment which such units create.

In order to address these problems, dentists currently employ aspiration devices to remove contaminants from the patient's mouth. Such devices generally are used in connection with spray jets which flush the work area with water or other fluid. The water is then drawn from the patient's mouth by the aspiration device and deposited in a collection tank. Contaminants which have been released into the patient's mouth thus are diluted, but may not be completely removed. This arrangement, however, fails to deal with the problem of harmful or infectious materials (i.e., bacteria, viruses and pathogens) which may be drawn into the turbine and released into the atmosphere through the handpiece's fluid output. Further, release of any contaminants into a patient's mouth is undesirable, even if the contaminants are subsequently removed. What is needed is a system which prevents harmful contaminants from entering the patient's mouth by drawing such contaminants into the handpiece flow path. Such contaminants then may be drawn from the handpiece via a vacuum source and deposited in a waste collector, avoiding contamination of the dental office environment.

DISCLOSURE OF THE INVENTION

The aforementioned problems are addressed by provision of an exhaust control system which has been adapted for use with one or more pneumatic devices so as to draw contaminated fluid from the fluid outputs of such devices and deposit such contaminated fluid in a waste collector such as a drain. The system is configured for use with any conventional pneumatic device of the type which includes a pressurized fluid input, a turbine driven by fluid from such input, and a fluid output which exhausts fluid from the turbine. Fluid is directed from the fluid output of each pneumatic device to an exhaust manifold which includes a number of inflow ports corresponding to the number of devices serviced. The inflow ports connect to a depressurization chamber where the fluid pressure is lowered, and from which the fluid is drawn via a collective outflow port. Typically, the depressurization chamber is sized to reduce the flow pressure of the fluid as it passes through the exhaust manifold. The fluid is drawn from the exhaust manifold using a vacuum pump and then directed to a waste collector such as a drain. The exhaust manifold further may include a relief valve configured to temporarily open when the pressure within the depressurization chamber falls below a predetermined low pressure. Where the pneumatic device is not perfectly sealed, it is possible to introduce a decontaminating fluid into the device's fluid flow path by submersion of the device in such a fluid, the decontaminating fluid being drawn into the flow path through leaks or openings in the handpiece, and directed into the waste drain via the vacuum pump.

A method of controlling exhaust from pneumatic devices thus may be considered to involve: 1) passing pressurized fluid through each pneumatic device so as to drive an onboard turbine, the pressurized fluid being contaminated; 2) directing such contaminated pressurized fluid from an output of the pneumatic device to an exhaust manifold which includes one or more inflow ports, each of which connects to a corresponding pneumatic device output; 3) depressurizing the contaminated pressurized fluid within a depressurization chamber of the exhaust manifold, the depressurization chamber receiving contaminated pressurized fluid from the inflow ports; 4) drawing depressurized contaminated fluid from the depressurization chamber via a vacuum source which is connected to the depressurization chamber via an outflow port; and 5) directing such drawn contaminated fluid through the vacuum source and into a waste drain. The aforementioned method also may involve opening of the depressurization chamber to an ambient atmosphere upon pressure within the depressurization chamber falling below a predetermined low pressure which is below the ambient atmospheric pressure, thereby increasing pressure within the depressurization chamber.

These and additional objects and advantages of the present invention will be more readily understood after a consideration of the drawings and the detailed description of the preferred embodiment which follows.

BRIEF DESCRIPTION OF THE DRAWINGS

FIG. 1 is a generally schematic representation of a dental unit which employs an exhaust control system including an exhaust manifold constructed in accordance with a preferred embodiment of the invention.

FIG. 2 is a side sectional view of the exhaust manifold depicted in FIG. 1.

FIG. 3 is an end view of the exhaust manifold depicted in FIG. 2.

FIG. 4 is a simplified fragmentary side sectional view of a dental handpiece of the type employed by the dental unit of FIG. 1.

DETAILED DESCRIPTION OF THE PREFERRED EMBODIMENT AND BEST MODE FOR CARRYING OUT THE INVENTION

Referring initially to FIG. 1, a preferred embodiment of the invented dental unit is shown, such unit being indicated generally at 10. In the depicted embodiment, dental unit 10 employs a control unit 12 which includes a pressurized fluid supply in the form of an onboard air compressor of the type used to drive pneumatic tools. The pressurized fluid supply similarly may take the form of an off-unit air compressor, or other device capable of providing fluid at a pressure sufficient to drive pneumatic tools (e.g., dental handpiece 14).

Dental unit 10 also employs a vacuum pump 16 which establishes a vacuum in an associated suction device such as that shown schematically at 15. Suction device 15 may take the form of a saliva ejector, a high volume expectorator, or any of a number of other suction tools. Such tools typically are configured to draw saliva from the patient's mouth during a dental procedure so as to keep the work area clear. The vacuum pump then deposits the material in a waste collector such as waste drain 18.

Dental unit 10 employs a series of pneumatic conduits 20–28, such conduits defining a flow path for fluid from control unit 12 to drain 18. For reasons which will be apparent, the conduits are non-collapsible, each taking the form of a nonporous tube configured to carry either a pressurized fluid or to support a vacuum. In the preferred embodiment, the conduits also are flexible, providing the dental unit operator with the ability to manipulate handpiece 14.

Referring still to FIG. 1, it will be noted that control unit 12 has a plurality of outputs, each output being connected to the onboard air compressor (not shown). Those skilled will appreciate that virtually any number of outputs may be employed, the number of outputs being limited primarily by the limitations of the air compressor and by the number of pneumatic tools. The control unit outputs thus supply pressurized fluid to input conduits 20a, 20b, 20c, each of which is connected to a pressurized fluid input of a corresponding pneumatic tool. Conduit 20a, for example, directs pressurized fluid to an input of handpiece 14.

As indicated in FIG. 4, handpiece 14 includes a fluid-driven turbine 14a which is configured to rotate upon supply of a pressurized fluid through conduit 20a. The turbine mounts on a shaft 14b which carries a dental bit B for use in connection with the treatment of a tooth T. Shaft 14b is rotatively mounted in the handpiece via a lubricated bearing arrangement 14c. Pressurized air thus may be supplied to engage vanes on turbine 14a, rotating the turbine, the shaft, and the associated dental bit. The pressurized fluid is then expelled through a pressurized fluid output via an output conduit 22a.

In the preferred embodiment, the dental unit will be seen to include a plurality of output conduits 22a, 22b, 22c, each of which is connected to a corresponding output of a handpiece such as that shown in FIG. 4. Typically, such output fluid is in some sense contaminated by operation of the handpiece, resulting in contaminated pressurized fluid output. Contaminants may, for example, include lubricants from the handpiece's bearing arrangement, or may include bacteria, viruses, pathogens or other undesirable products which could be present in the fluid from the fluid source, or may enter the flow path due to leaks or openings in the fluid path.

The output conduits connect to an exhaust manifold 30 which is fitted with a plurality of inflow ports as will be described below. The exhaust manifold serves to reduce the pressure of the fluid, the fluid being drawn from the manifold through a single outflow port via a manifold outflow conduit 24. The manifold outflow conduit, in turn, connects to a vacuum conduit 26 which runs between vacuum pump 16 and suction device 15. Such connection may be made by an appropriate intersection valve to introduce suction to conduit 24. The vacuum pump draws the fluid into the pump and expels the fluid into drain 18 via a waste conduit 28.

Referring now to FIGS. 2 and 3, a detailed illustration of the exhaust manifold is provided, such manifold including an elongate tube 32 with an interior depressurization chamber 34. Tube 32, it will be noted, has a plurality of radially-defined inflow ports in the form of openings 36a–36f. Each inflow port is fitted with either a coupling element 38a, 38b, 38c or a plug 38d, 38e, 38f. In the depicted embodiment, inflow ports 36a, 36b, 36c are fitted with corresponding coupling elements 38a, 38b, 38c which connect to conduits 22a, 22b, 22c. Inflow ports 36d, 36e, 36f are unused, and thus are fitted with plugs 38d, 38e, 38f.

The manifold further may be adapted to connect to additional pneumatic tools by removal of the plugs, and insertion of corresponding coupling elements. It thus will be appreciated that the depicted exhaust manifold is adaptable for use in connection with as many as six different pneumatic tools. It similarly is adaptable for use with a single pneumatic tool. Both the coupling elements and the plugs are threaded so as to provide for sealed engagement with correspondingly threaded openings 36a–36f. Hex bolt heads facilitate installation and removal of the coupling elements and plugs.

In the preferred embodiment, tube 32 is closed on opposite ends by end caps 32a, 32b which are applied to opposite ends of the tube via an adhesive such as conventional pipe cement. Both the tube and end caps, it will be understood, typically are formed from a conventional pipe material such as PVC. Cap 32a has a longitudinally-defined outflow port in the form of an opening 33 which connects directly to depressurization chamber 34. A coupling element 40 is threadedly seated within opening 33, providing for connection of the outflow port to conduit 24. Exhaust manifold 30 thus provides for flow of fluid through inflow ports 36a–36c to depressurization chamber 34, and then through a single collective outflow port 33.

Depressurization chamber 34 is sized to provide for depressurization of the input fluid, such fluid being drawn from the chamber by vacuum pump 16. This is accomplished by providing a depressurization chamber which has a cross-sectional area which is greater than the cross-sectional area of any of the inflow or outflow ports. This is best illustrated in FIG. 3. Such arrangement avoids forcing pressurized fluid into the vacuum pump, potentially damaging such vacuum pump.

Referring to FIG. 2, it will be noted that cap 32b has a longitudinally-defined relief port 35 which carries a relief valve in the form of Schraeder valve 42. Valve 42 is normally closed, but is configured to open upon the pressure within the depressurization chamber falling below a predetermined low pressure which is lower than ambient pressure. When the valve opens, air is drawn into the flow path as indicate at 42a, the pressure within the depressurization chamber being increased so as to avoid excessive suction through conduits 22a, 22b, 22c, an event which would tend to cause the turbine of the handpiece to turn and/or excessive noise in the handpiece. In the preferred embodiment, valve 42 is adjustable so as to provide for varying degrees of suction through conduits 22a, 22b, 22c.

Referring once again to FIG. 4, it is noted that handpiece 14 has leaks or openings such as the opening through which the device's bit extends. Contaminants from the patient's mouth may be drawn through such opening into the flow path, and contaminants from the handpiece (including bacteria, viruses, pathogens or other contaminants from the fluid source) may be inadvertently expelled into the patient's mouth. Previous dental units typically would release the fluid from the flow path into the air, resulting in a generally unsanitary environment. Dental unit 10, however, provides a vacuum pump which constantly draws contaminants from the flow path, and which may be configured to draw a sterilization fluid through the handpiece so as to purge the system of contaminants. This purge is accomplished by submerging the handpiece in a sterilization fluid, such fluid being drawn through the openings in the handpiece as indicated at 44. The fluid is pulled through output conduit 22a, into exhaust manifold 30, and through the vacuum pump for deposit in waste drain 16. Further, handpiece 14 may include coolant tubes (not shown) which deliver a coolant fluid to the work area, and which similarly may be decontaminated using a secondary exhaust manifold.

The method followed to control exhaust from the pneumatic tools thus may be considered to involve: 1) passing pressurized fluid through each pneumatic device so as to drive an onboard turbine, the pressurized fluid being contaminated; 2) directing such contaminated pressurized fluid from an output of the pneumatic device to an exhaust manifold which includes one or more inflow ports, each of which connects to a corresponding pneumatic device output; 3) depressurizing the contaminated pressurized fluid within a depressurization chamber of the exhaust manifold, the depressurization chamber receiving contaminated pressurized fluid from the inflow ports; 4) drawing depressurized contaminated fluid from the depressurization chamber via a vacuum source which is connected to the depressurization chamber via an outflow port; and 5) directing such drawn contaminated fluid through the vacuum source and into a waste drain. The aforementioned method also may involve opening of the depressurization chamber to an ambient atmosphere upon pressure within the depressurization chamber falling below a predetermined low pressure which is below the ambient atmospheric pressure, thereby increasing pressure within the depressurization chamber.

INDUSTRIAL APPLICABILITY

The present invention is shown and described above in connection with a dental unit having a plurality of pneumatic tools in the for of dental handpieces. It will be appreciated, however, that the invented exhaust control system similarly may be employed in connection with various pneumatic devices to direct exhaust into a waste drain rather than into the atmosphere as is conventional. Further, while the present invention has been shown and described with reference to the foregoing operational principles and preferred embodiment, it will be apparent to those skilled in the art that various changes in form and detail may be made without departing from the spirit and scope of the invention as defined by the claims.

I claim:

1. An exhaust control system for use with one or more pneumatic devices, each of which has a pressurized fluid input, a turbine driven by fluid from such fluid input and a fluid output which exhausts contaminated fluid from the turbine, said exhaust control system comprising:
   an exhaust manifold including a plurality of inflow ports, each having structure for connecting an output of a corresponding pneumatic device, said exhaust manifold providing a depressurization chamber through which contaminated fluid flows downstream to a collective overflow port, said depressurization chamber being sized to reduce pressure of the contaminated fluid as such contaminated fluid flows through the depressurization chamber;
   a vacuum source connected to said collective outflow port to draw contaminated fluid from said exhaust manifold, said vacuum source being configured to direct the drawn contaminated fluid to a waste collector.

2. The exhaust control system of claim 1, wherein said exhaust manifold further includes a relief valve.

3. The exhaust control system of claim 2, wherein said relief valve is configured to temporarily open upon pressure within said depressurization chamber falling below a predetermined low pressure.

4. The exhaust control system of claim 2, wherein said relief valve is adjustable, said relief valve being configurable to temporarily open upon pressure within said depressurization chamber falling to a selected pressure.

5. The exhaust control system of claim 1, wherein said depressurization chamber has a first cross-sectional area, and said inflow and outflow ports each have a second cross-sectional area, said first cross-sectional area being greater than any of said second cross-sectional areas.

6. The exhaust control system of claim 1, wherein said exhaust manifold is an elongate tube having a plurality of radially-defined inflow ports and a single longitudinally-defined outflow port.

7. The exhaust control system of claim 6, wherein said exhaust manifold further includes a relief valve opposite said outflow port, said relief valve extending longitudinally between an exterior of said exhaust manifold and said depressurization chamber.

8. The exhaust control system of claim 6 which further comprises one or more plugs configured to selectively close unused inflow ports.

9. The exhaust control system of claim 1, wherein said waste collector is a drain.

10. A dental unit comprising:
    an air compressor configured to provide pressurized air;
    one or more pneumatic handpieces, each defining a flow path including an input which receives pressurized air from said air compressor, a turbine driven by said pressurized air, and an output which exhausts contaminated air from the turbine;
    an exhaust manifold including one or more inflow ports, each of which connects to an output of a corresponding pneumatic handpiece, said exhaust manifold providing a depressurization chamber through which contaminated air flows downstream to a single outflow port, said depressurization chamber being sized to reduce pressure of the contaminated air as such contaminated air flows through said depressurization chamber;
    a vacuum pump connected to said outflow port to draw contaminated air from said depressurization chamber, said vacuum pump being configured to direct such drawn contaminated air to a waste drain.

11. The dental unit of claim 10, wherein said exhaust manifold further includes a relief valve configured to temporarily open said depressurization chamber to an ambient atmosphere upon pressure within said depressurization chamber falling below a predetermined low pressure which is below an ambient atmospheric pressure, thereby increasing pressure within said depressurization chamber.

12. The dental unit of claim 11, wherein said relief valve is adjustable to vary said predetermined low pressure.

13. The dental unit of claim 10, wherein said exhaust manifold is an elongate tube having a plurality of radially-defined inflow ports, a longitudinally-defined outflow port, and a longitudinally-defined relief valve opposite said outflow port, said relief valve connecting said depressurization chamber with an ambient atmosphere.

14. The dental unit of claim 10, wherein said depressurization chamber has a first flow capacity, and said inflow and outflow ports each have substantially equal second flow capacities, said first flow capacity being greater than any of said second flow capacities.

15. The dental unit of claim 10, wherein at least one of said pneumatic handpieces provides for introduction of a decontaminating fluid into its flow path, said decontaminating fluid being drawn into said flow path and directed to a waste drain via said vacuum pump.

16. The dental unit of claim 15, wherein said pneumatic handpiece defines one or more seepage openings through which decontaminating fluid may be drawn into said flow path.

17. The dental unit of claim 16, wherein said sterilization fluid is introduced into said flow path by at least partial submersion of said pneumatic handpiece into said decontaminating fluid.

18. A method of controlling exhaust from one or more pneumatic handpieces of a dental unit, said method comprising the steps of:

passing pressurized air through each pneumatic handpiece to drive an onboard turbine, the pressurized air being contaminated;

directing such contaminated pressurized air from an output of the handpiece to an exhaust manifold which includes one or more inflow ports, each of which connects to a corresponding handpiece output;

depressurizing the contaminated pressurized air within a depressurization chamber of the exhaust manifold, the depressurization chamber receiving contaminated pressurized air from the inflow ports;

drawing depressurized contaminated air from the depressurization chamber via a vacuum pump, the vacuum pump being connected to the depressurization chamber via a single outflow port; and directing such drawn contaminated air through the vacuum pump and into a waste drain.

19. The method of claim 18 which further comprises temporarily opening the depressurization chamber to an ambient atmosphere via a relief valve upon pressure within the depressurization chamber falling below a predetermined low pressure which is below ambient atmospheric pressure, thereby increasing pressure within the depressurization chamber.

20. The method of claim 18 which further comprises introducing a decontaminating fluid into the handpiece, the decontaminating fluid being drawn into the handpiece, through the exhaust manifold, and into the waste drain via the vacuum pump.

* * * * *